US00PP09476P

United States Patent [19]

Kent

[11] Patent Number: Plant 9,476

[45] Date of Patent: Mar. 12, 1996

[54] BROMELIAD PLANT NAMED 'GUZ 214'

[75] Inventor: Jeffrey C. Kent, Vista, Calif.

[73] Assignee: Kent's Bromeliad Nursery, Inc., Vista, Calif.

[21] Appl. No.: 364,596

[22] Filed: Dec. 27, 1994

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Frank B. Robb; Robb & Robb

[57] ABSTRACT

A new and distinct bromeliad cultivar of the Guzmania family which produces bracts of a strong amaranth color which color commonly lasts three months, the leaves of the plant being variegated with strong white color throughout setting off the bract coloration not found in any known bromeliad.

1 Drawing Sheet

GENERAL DESCRIPTION OF THE INVENTION

This invention relates to bromeliads in general and specifically to one of the genus called Guzmania and a particular one which is designated by me as Bromeliad named 'GUZ 214' which will identify it in commerce.

As is known to those skilled in the art, bromeliads generally are called bromeliaceae and in particular it is noted that this is a large family of tropical American plants which interestingly enough is of the pineapple family. Bromeliads generally are said to comprise about 40 genera and over 900 species, which indicates that there is a wide variety of color, form, and name, for plants of this nature.

Particularly in this instance I have concentrated my efforts in developing bromeliads, of the Guzmania genus and as indicated have found that it has some interesting characteristics which make it a desirable commercial plant.

The botanical class Bromeliaceae, which includes Guzmania, contains member genera which are generally quite showy but which differ largely in coloration, shape and size. Plants of the botanical and market class Guzmania have a number of characteristics in common which make them recognizable as bromeliads by those skilled in the art. Notably, members of Guzmania, are desirable for their pleasing ornamental appearance which is tropical and exotic; their durability as flowering indoor ornamental specimen plants; and, the outstanding duration of their highly colored inflorescence, which may extend for periods of about 3 months or more.

The particular Guzmania plant of this invention resulted from a spontaneous mutation of one plant within a large population of plants of a monoculture of the parent variety 'Amaranth' which was being commercially produced under my direction. This plant was conspicuously different due to the interesting variegation of its foliage which differed from the generally solid green leaves of the remainder of the plants of the population. The plant of the invention otherwise remains similar to the normal plants in terms of shape, size and flower characteristics.

The particular plant herein disclosed and described as discovered by me growing in a greenhouse under my control, is a perennial developing an overall height of 20 to 22 inches which include the inflorescence.

The plant is of a substantial width, about 26 inches at full growth and has interestingly long, relatively narrow leaves which may extend for 16 to 18 inches and are generally of a width of 1 inch.

The leaves of this plant are variegated longitudinally and express a contrasting central variegation band which is predominantly white to light green in color and contains plural dark green streaks of the same shade as the dark green margins. The green stripes follow veins within the central white to light green variegation band. The basal portions of the newest leaves of specimens induced to flower are flushed with amaranth 40. This deep red shading may extend to about one-half, or more, progressively, of the length of the newest true leaves which are formed directly below the floral bracts of this plant.

The floral bracts are of linear shape and have acuminate tips, and are normally shorter than the true leaves; but have a more flaring rather than ascending orientation. The length of the bracts is variable, but may range to about seven inches, for the oldest bracts, with newly forming bracts being of progressively shorter length. The bract width is about as wide as that of the true leaves, or about one inch. The bracts of this plant flare outwardly to a wider angle than do the newest leaves, and are attractively and solidly colored amaranth 40, matching the basal shading of the newest leaves. At optimum inflorescence, bracts at the apex of the spike of the inflorescence are typically about two and three-quarters inches long by three-quarters of an inch width, with acuminate tips and entire margins. The unique and attractive combination of leaf variegations, which are the attractively contrasting central white and marginal deep green color banding, with the dense red bract coloration results in a plant having exceptional attractiveness, and potential market acceptance.

In order to disclose the plant in the form which it has developed and in which it has been reproduced by asexual propagation over several generations, I have found that as the sport appeared it continues to maintain the characteristics thereof over the time and over subsequent division of the plant.

Asexual reproduction is carried out by division and I have caused that to take place under my direction near my greenhouses in the area of Vista, Calif. The parent plant 'Amaranth' of this sport is a commercially available plant and the color and morphology of the flower parts of this plant are identical to those of the parent plant.

BRIEF DESCRIPTION OF THE DRAWING

In order to disclose the plant and its coloration, I show the same in the drawing appended hereto which discloses the same in as near a replication of the plant as is possible by photographic processes and characteristic of the plant although obviously it is a photograph that is the basis for the description.

Color values presented in this disclosure were taken from the *Horticultural Color Guide* as presented in *Exotica.* Such color definitions are based on the *Dictionary of Color* by Maerz & Paul. Color definitions of ordinary meaning are presented where appropriate and properly descriptive.

BOTANICAL DESCRIPTION OF THE PLANT

In order to specifically describe many of the different aspects of the plant, I append hereto additional specific description with comments carried therethrough.

Plant classification:

*Botanical.*—Spontaneous Guzmania mutation.

*Commercial.*—Flowering tropical plant of the guzmania market class.

Parentage: Spontaneous mutation of the commercial variety 'Amaranth'. Method of asexual reproduction: Division.

PLANT

General characteristics:

*Type.*—Monocot, perennial.

*Habit.*—Single stem, whorled and closely spaced ascending linear, strap-like leaves with acuminate terminals, typical of hybrids of Guzmania and market class guzmania plants. Lower leaves may droop with age if plant is not timely induced to flower. Terminal portions of most mature leaves may droop in a graceful arch. Internode length and spike length may be more elongated with culture under low light levels or high levels of nitrogen fertilization.

*Hardiness.*—Tender, tropical.

*Size.*—About 26 inches, or more, in width, with the ultimate height determined by the timing of gas induction of flowering. Plant height for optimum marketing is about 18 to 19 inches, or taller, including the inflorescence.

*Shape.*—Normally mounded, generally typical of plants of the genus. Leaf placement is whorled forming a rosette.

*Density.*—Leaf spacing is typically close, and typical of hybrids of the market class. Leaf spacing and internode length may increase with culture under low light conditions or when too much nitrogen fertilizer is applied.

*Vigor.*—Considered vigorous, but has less vigor than the parent 'Amaranth' due to the overall chlorophyll content of the variegated leaves.

*Leaves.*—Linear, elongated, ranging to about 16 to 18 inches, or longer, as a function of cultural conditions. Leaves are ivy green 70 variegated with a central, predominately white to light green band. The white strip of variegation may contain a plurality of distinct green strips which follow veins. Marginal zones of leaves are solid, deep green bands which commonly comprise about one-fourth of the width of the leaf lamina. Leaves have acuminate tips. Thickness is about normal for that of plants of this market class. Surfaces are smooth and semi-glossy. Margins are complete (smooth); leaves are straight when newly formed, but become gently arched when elongated.

Flower buds: Tender, medium and long in size, pointed, and appressed, white, 3/16"×1¼".

Floral bracts:

*Color.*—Amaranth (40) on obverse and reverse, and lasts up to three months

Flowers: Cylindrical corolla, white at anthesis, flower petals barely open at anthesis, white, 3/16"×1¼".

Reproductive organs: Six stamens, two joined to each petal ¼ of the distance from the base, stigmata white, sterile $F^1$ hybrid.

SUMMARY

As a commercial bromeliad the instant variety after discovery has continued to be grown for the colors, shape and size of the floral bracts. The strong amaranth color of the bracts of this plant is well set off by the striking white variegation of the leaves, the color of the bracts usually lasts up to three months, there being no known commercial bromeliad of these colors and leaf variegation.

I claim:

1. A new and distinct Bromelioad plant, substantially as herein shown and described, characterised particularly as to novelty, by the strong amaranth color of the bracts, the long lasting color of the bracts which characteristically lasts for periods up to three months and the striking white variegation of the leaves.

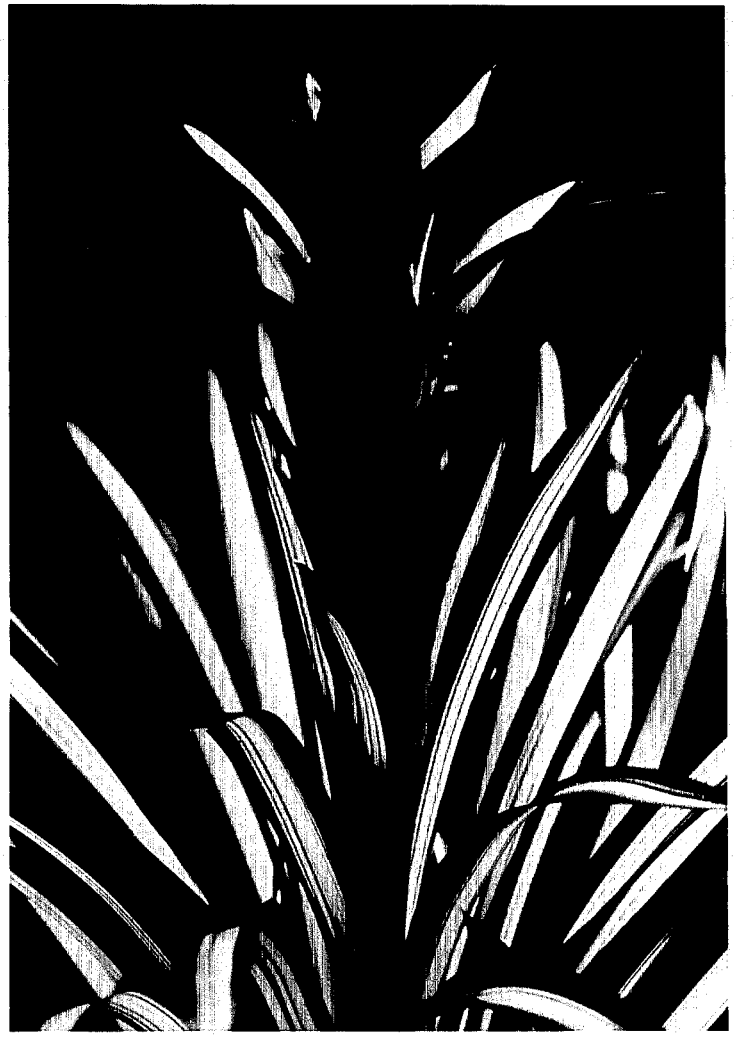

* * * * *